(12) United States Patent
Dutt et al.

(10) Patent No.: US 12,347,557 B2
(45) Date of Patent: Jul. 1, 2025

(54) DEEP NEURAL NETWORK (DNN) ASSISTED SENSOR FOR ENERGY-EFFICIENT ELECTROCARDIOGRAM (ECG) MONITORING

(71) Applicant: THE REGENTS OF THE UNIVERSITY OF CALIFORNIA, Oakland, CA (US)

(72) Inventors: Nikil Dutt, Irvine, CA (US); Tao-Yi Lee, Irvine, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 313 days.

(21) Appl. No.: 17/108,494

(22) Filed: Dec. 1, 2020

(65) Prior Publication Data
US 2021/0174961 A1   Jun. 10, 2021

Related U.S. Application Data

(60) Provisional application No. 62/945,655, filed on Dec. 9, 2019.

(51) Int. Cl.
  *G16H 50/00*  (2018.01)
  *A61B 5/00*  (2006.01)
  *G16H 40/67*  (2018.01)
  *G16H 50/20*  (2018.01)

(52) U.S. Cl.
  CPC .......... *G16H 50/20* (2018.01); *A61B 5/0006* (2013.01); *A61B 5/7267* (2013.01); *G16H 40/67* (2018.01)

(58) Field of Classification Search
  None
  See application file for complete search history.

(56) References Cited

U.S. PATENT DOCUMENTS

| | | | |
|---|---|---|---|
| 9,468,386 B2 * | 10/2016 | Braojos Lopez | A61B 5/349 |
| 10,602,942 B2 * | 3/2020 | Shakur | A61B 5/349 |
| 2014/0142448 A1 * | 5/2014 | Bae | A61B 5/349 |
| | | | 600/515 |

(Continued)

FOREIGN PATENT DOCUMENTS

JP       7070255 B2 *  5/2022  ............. A61B 5/363

OTHER PUBLICATIONS

Jin et al., Ensemble Deep Learning for Biomedical Time Series Classification, 2016 (Year: 2016).*
Neural Networks, OBGYN, Stats (Year: 2002).*

*Primary Examiner* — Sana Sahand
(74) *Attorney, Agent, or Firm* — NGUYEN TARBET IP LAW

(57) ABSTRACT

The present invention is directed to an energy-efficient method of monitoring a physiological signal while maintaining high accuracy. The method may comprise a Deep Neural Network (DNN) receiving an uncompressed sample of a continuous ECG signal from a sensor. The method may further comprise the DNN determining a first probability that the received sample is abnormal and a second probability that the received sample is normal. Finally, the method may further comprise the DNN determining to transmit the uncompressed sample if a threshold of abnormality is less than or equal to the difference between the first probability and the second probability. In some embodiments, the DNN may be a Convolutional Neural Network (CNN).

6 Claims, 16 Drawing Sheets

Fig. 2. Two representative architectures of CNN employed in this work. Layer caption "Conv1D(α, β)" denotes a 1D convolution layer which has α filter kernels (channels) and β filter length; "Dropout(γ)" denotes dropout [14] layer with rate of γ.

(56) References Cited

U.S. PATENT DOCUMENTS

| | | | |
|---|---|---|---|
| 2017/0112401 A1* | 4/2017 | Rapin | A61B 5/7267 |
| 2018/0116537 A1* | 5/2018 | Sullivan | A61N 1/046 |
| 2019/0069795 A1* | 3/2019 | Kiranya | G16H 50/20 |
| 2019/0361140 A1* | 11/2019 | Lee | G01V 3/28 |
| 2019/0374166 A1* | 12/2019 | Charles | A61B 5/0006 |
| 2020/0074281 A1* | 3/2020 | Dindin | A61B 5/364 |
| 2020/0205687 A1* | 7/2020 | Rubin | G16H 40/63 |
| 2021/0153761 A1* | 5/2021 | Jung | A61B 5/7264 |

* cited by examiner

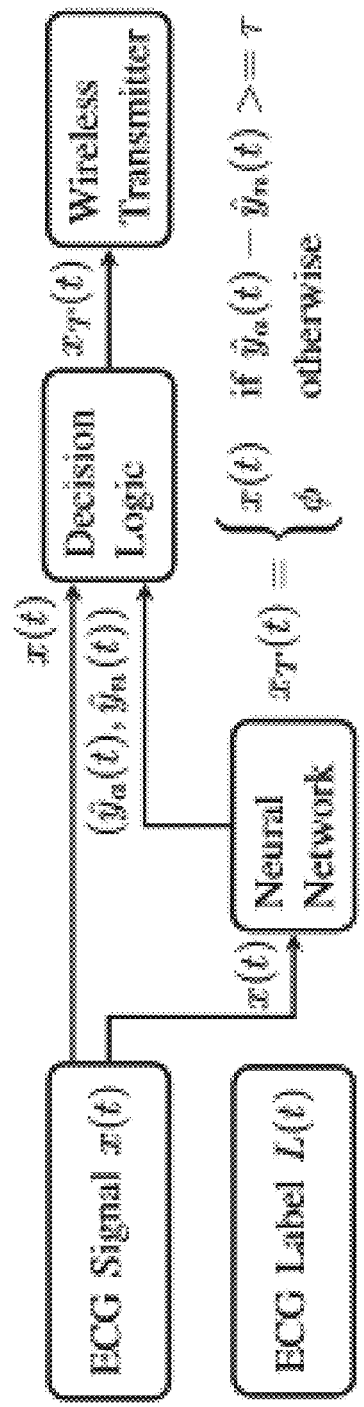
Fig. 1. Schematics of the proposed system.

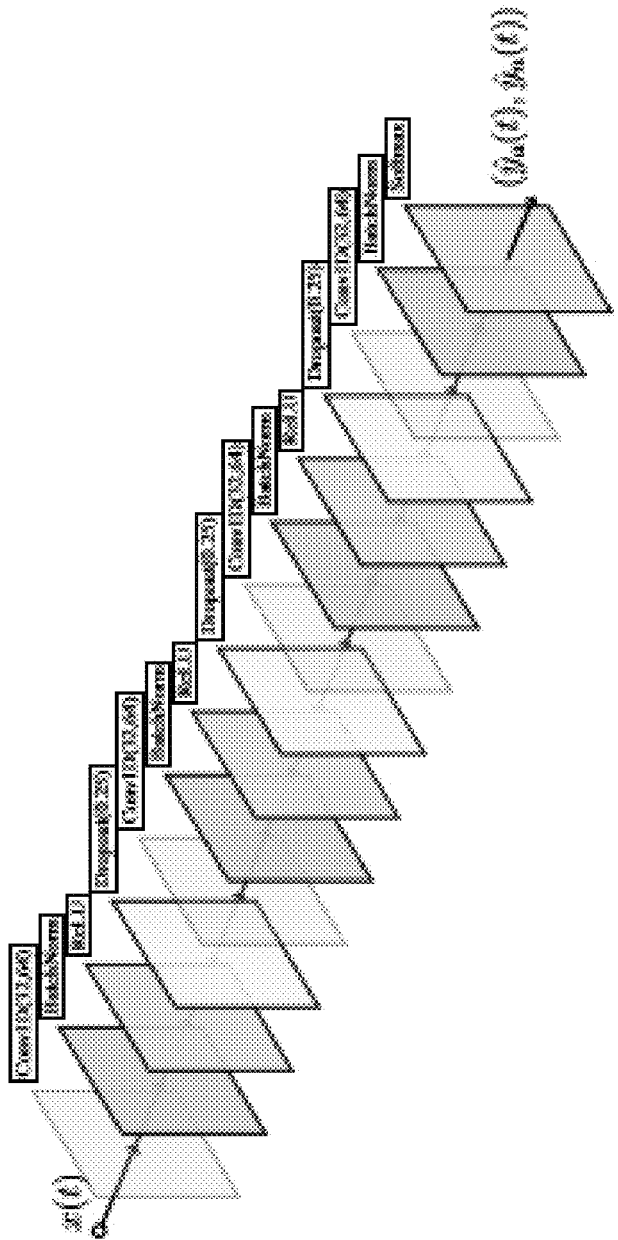
Fig. 2. Two representative architectures of CNN employed in this work. Layer caption "Conv1D($\alpha$, $\beta$)" denotes a 1D convolution layer which has $\alpha$ filter kernels (channels) and $\beta$ filter length; "Dropout($\gamma$)" denotes dropout[14] layer with rate of $\gamma$.

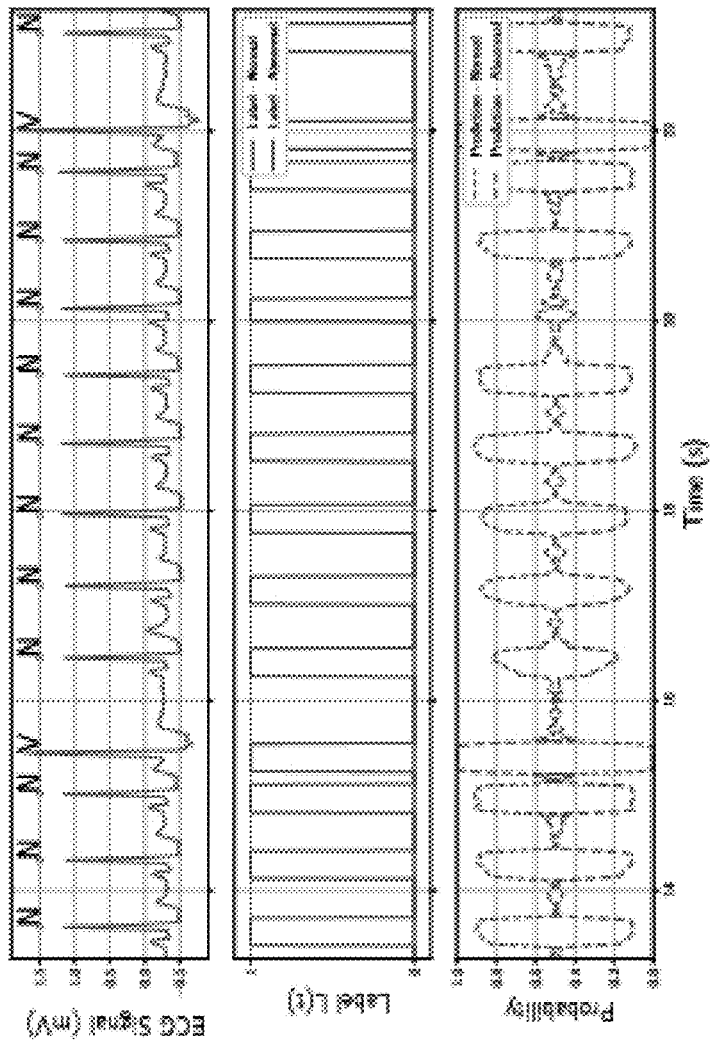

Fig. 3. Inference results on MITDB record number 105 via CNN which has 137,510 parameters. Blue curve is the Modified lead II (MLII) signal. Note that two VPC events, indicated by symbol "V", are observed in this interval. Middle panel shows the label which is derived from annotation files; Bottom panel shows prediction outputs for normal $\hat{y}_n(t)$ and abnormal heartbeats $\hat{y}_a(t)$.

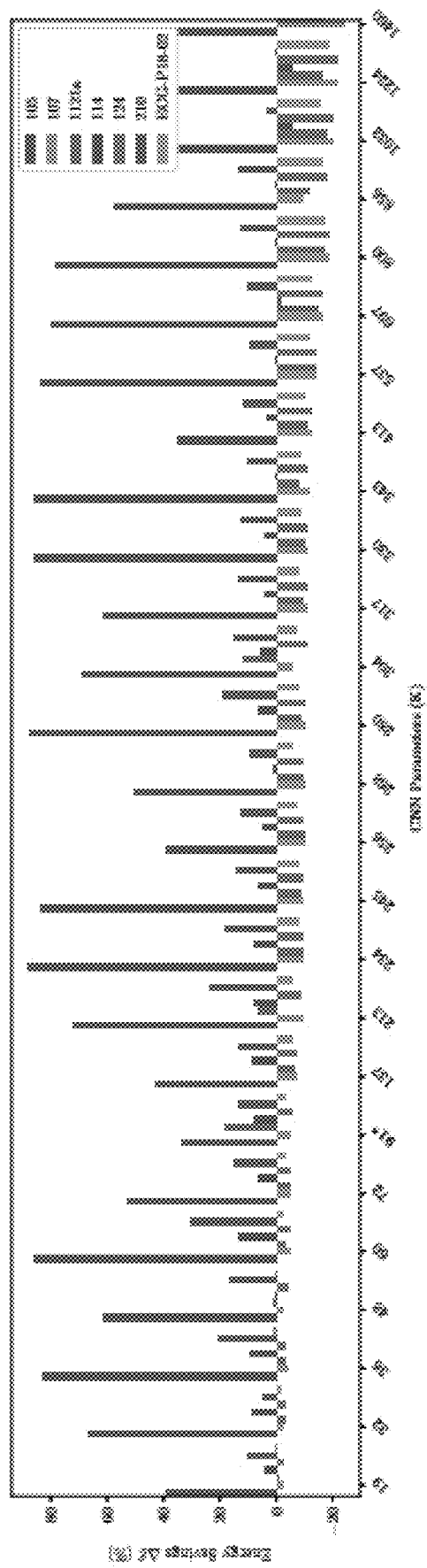
Fig. 4. Achievable energy saving among all CNN

Fig. 5. Mistransmission rate among 6 test records. Real data points are indicated by black dots. Any single point on the left contour has a corresponding point on the right. Lower threshold value τ (color coded blue) corresponds to a more conservative DNN which leads to more data transmission.

Fig. 6. Mistransmission per record.

Figure 12

- View ECG signal as a time series $x(t)$
- Define two metrics
  - Bandwidth utilization (1/Compression ratio) ⟵ Goal: Minimize $$b_{tx} = \frac{|\{x_i : x_i \in x_T(t) \land x_T \neq \phi\}|}{|\{x_i : x_i \in x(t) \land x \neq \phi\}|}$$

- Mistransmission rate (How many positive samples are dropped?) ⟵ Goal: Minimize $$c_{mt} = \frac{|\{x_i : x_i \in x_T(t) \land L(t_i) = (1,0)\}|}{|\{x_i : x_i \in x(t) \land L(t_i) = (1,0)\}|}$$

- 20 CNN with different complexities are trained to detect arrhythmia
- Performance metrics evaluated under different decision thresholds
- Dataset consists of 205 records
  - training/testing = 198/7

Figure 15

| Record | $\Delta\varepsilon$ (%) | $\tau$ | $b_{t,x}$ (%) |
|---|---|---|---|
| 105 | 33.91 | -0.14 | 59.71 |
| 1121a | 18.12 | 0.03 | 75.50 |
| 210 | 13.47 | -0.44 | 80.15 |
| 114 | 8.48 | -0.56 | 85.15 |
| ECG-P18-02 | -3.65 | -0.72 | 97.28 |
| 107 | -4.75 | -0.14 | 98.37 |
| 124 | -5.65 | -0.81 | 99.28 |

With additional DNN, 33.9% energy savings can be achieved on the sensors

DEEP NEURAL NETWORK (DNN) ASSISTED SENSOR FOR ENERGY-EFFICIENT ELECTROCARDIOGRAM (ECG) MONITORING

CROSS-REFERENCES TO RELATED APPLICATIONS

This application is a non-provisional and claims benefit of U.S. Provisional Application No. 62/945,655 filed Dec. 9, 2019, the specification of which is incorporated herein in their entirety by reference.

BACKGROUND OF THE INVENTION

After more than a century since it was first invented, the electrocardiogram (ECG) has become a commodity cardiovascular disease (CVD) diagnostic tool. Nowadays, the acquisition of ECG signals can be performed by wearable devices. The availability of ECG signals enables a broad spectrum of applications, ranging from early detection of premonitory signs of myocardial ischemia and arrhythmia to long term monitoring for the identification of rare but life-threatening rhythms. Recent contributions by Hannun et. al. [2] have demonstrated cardiologist-level detection and classification of arrhythmia by means of specialized convolutional neural networks (CNN).

One existing clinical device, the Holter monitor, allows continuous acquisition of ECG signals for extended time periods. However, due to the sheer amount of data, expert interpretation of Holter readings is often performed offline, sometimes severely delayed. Furthermore, some features in ECG recording which suggest heart malfunction only appear infrequently. For instance, premature ventricular contractions (PVCs) is an elusive rhythm which might lead to the diagnosis of heart failure (HF) and cardiomyopathy. According to [3], 24-hour or 48-hour Holter monitoring is usually prescribed to identify a key determinant of PVC—ventricular premature beats (VPB)—when a patient complains of dizziness or palpitations after there were no specific findings in routine 12-lead ECG. Events of VPB might occur as infrequently as once a week or even a couple of times a month [4]. Naively transmitting and recording complete ECG signals seems to be wasteful in dealing with such rare rhythms.

Therefore, it is assumed there exists a way to efficiently collect and deliver ECG signals to the final analysis unit without employing a high-capacity communication channel. In other words, current wireless transceivers have potential to support more sensors without any increase of the energy budget.

ECGs are amenable to compression techniques due to their quasi-periodicity, but compression must be applied carefully to avoid any distortion of features instrumental to classification. In fact, while Deep Neural Networks (DNN) appear to be an ideal tool to analyze ECG signals at the clinical level, this family of tools requires a high precision representation of the full morphology of the signal. Several works have explored compression techniques to mitigate this bandwidth requirement. The most relevant to the systems investigated herein is compressive sensing (CS). CS exploits the repetitive nature of ECG and employs l1-minimization to approximate raw signals using a sparse reconstruction matrix with minimum distortion. To obtain sparse representation of ECG, wavelet transforms[8] and dictionary learning[9] are commonly adopted. Other approaches to obtain a high-fidelity signal recovery, such as auto-encoders [10], are often too complex to be executed in-sensor.

The main limitation of traditional compression approaches is that they aim to generate a high-quality reconstruction of the entire signal. This necessarily results in a large amount of storage and/or channel capacity needed to represent normal rhythms, which may be useless for the final diagnosis objective, which only requires anomalous rhythms. Here, the different approach of "pre-selecting" interesting and potentially anomalous portions of the ECG signals is taken, by completely removing uninformative normal heart cycles from the signal representation. To this aim, a deep neural network (DNN) that is executed at the sensor and which provides as output the probability that a rhythm is anomalous is trained. A threshold strategy is then used to determine whether or not the rhythm is transmitted and stored. Intuitively, the execution of complex DNNs, such as those providing fine-grain classification of ECG cycles, is likely infeasible on wearable sensors. Thus, herein a thorough evaluation of a wide range of DNN parameters is provided to explore the tradeoff between complexity/energy consumption, channel usage, and diagnosis accuracy.

The rest of the paper is organized as follows. Section II begins by formulating a quantitative framework that evaluates how well the system performs in terms of mistransmission rate and normalized energy cost. Section III presents a detailed description of the proposed system and its critical functional blocks. Section V presents experimental results to numerically validate the proposed methods using a parameterized CNN energy estimation model. Section VI concludes the paper.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 1 shows the schematics of the proposed system (basic architecture).

FIG. 2 shows two representative architectures of Convolutional Neural Network (CNN) employed in this work. Layer caption "Conv1D($\alpha$, $\beta$)" denotes a 1D convolution layer which has $\alpha$ filter kernels (channels) and $\beta$ filter length; "Dropout($\gamma$)" denotes dropout layer with a rate of $\gamma$.

FIG. 3 shows inference results on MITDB record number 105 via CNN which has 137,510 parameters. Blue curve in the Modified lead II (MLII) signal. Note that two VPC events, indicated by symbol "V," are observed in this interval. The middle panel shows the label which is derived from annotation files. The bottom panel shows prediction outputs for normal $\hat{\gamma}_n(t)$ and abnormal $\hat{\gamma}_n$ heartbeats.

FIG. 4 shows achievable energy savings among all CNN.

Figure 5:
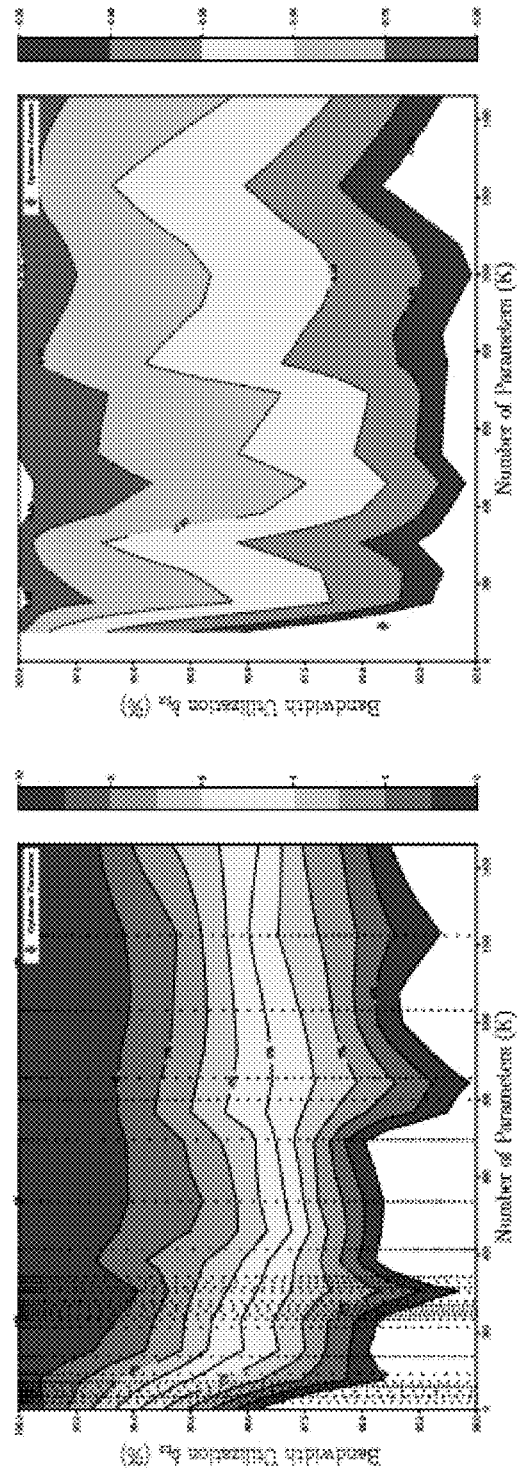

FIG. 5 shows mistransmission rate among 6 test records, Real data points are indicated by black dots. Two subplots should be read relationally. Any single point on the left contour has a corresponding point on the right, Lower threshold value T (color-coded blue) corresponds to a more conservative DNN which leads to more data transmission.

Figure 6:
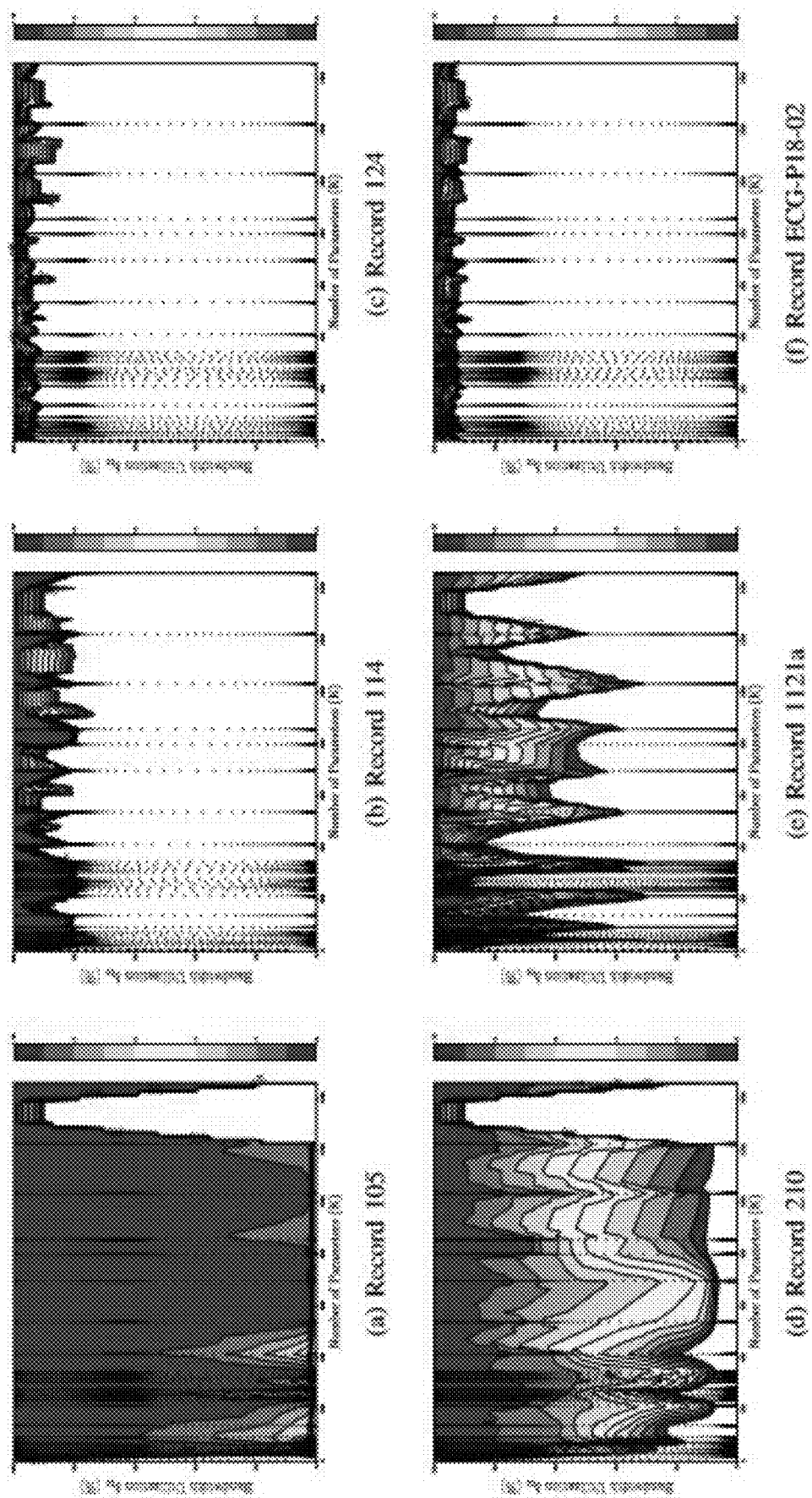

FIG. 6 shows mistransmission per record.

Figure 7:
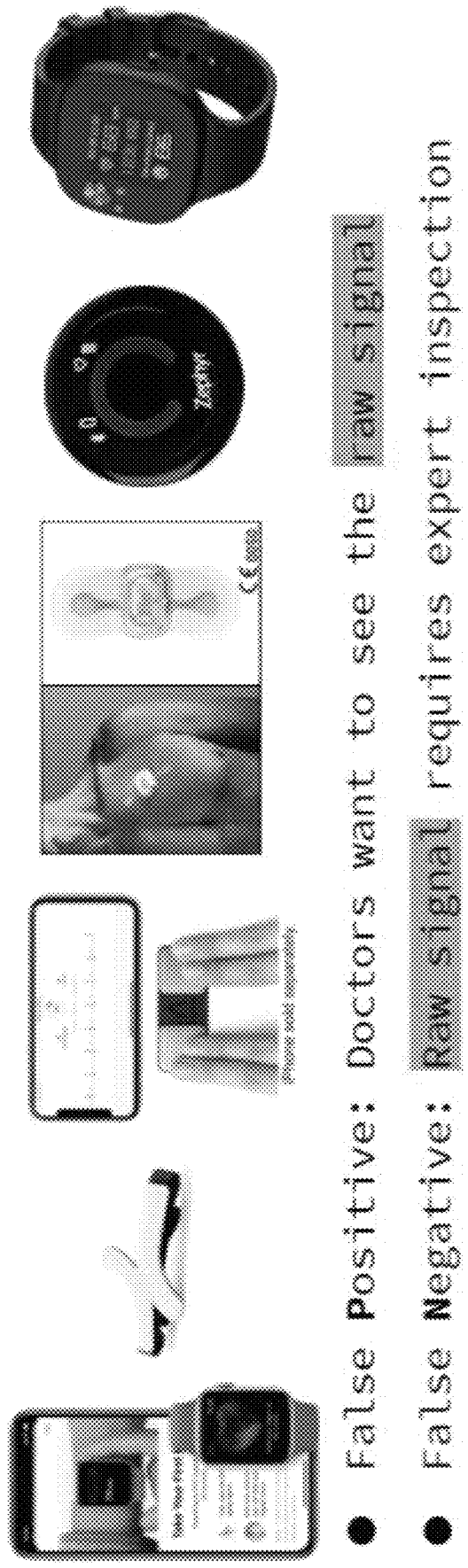

FIG. 7 shows various wearable ECG's and the reasons that machine learning would benefit these devices.

Figure 8:
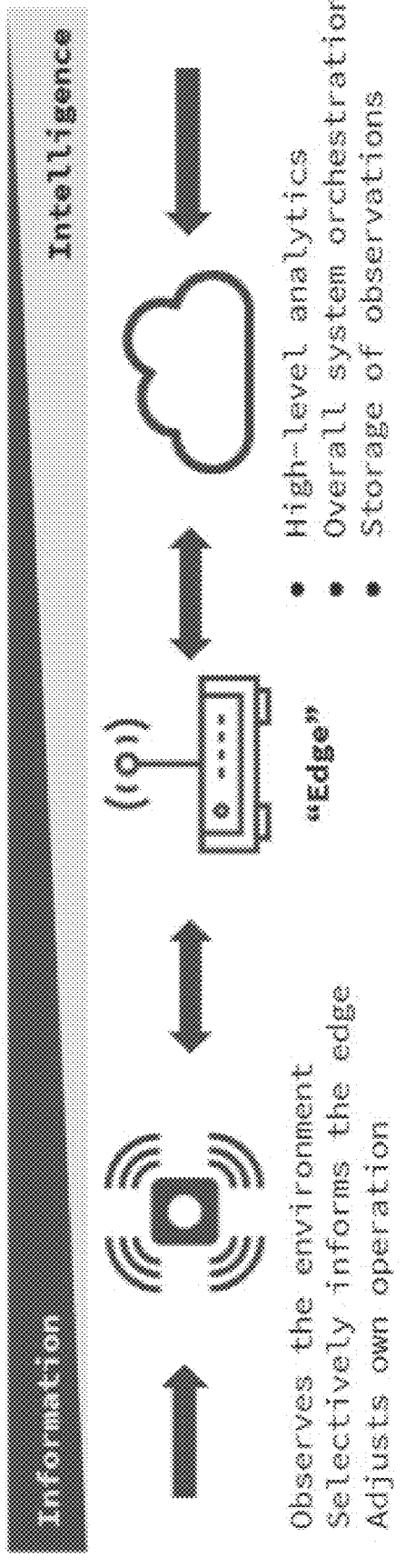

FIG. 8 shows related works: compressive sensing and fog computing (edge-assisted computing) with a diagram that outlines the fog computing process.

Figure 9:
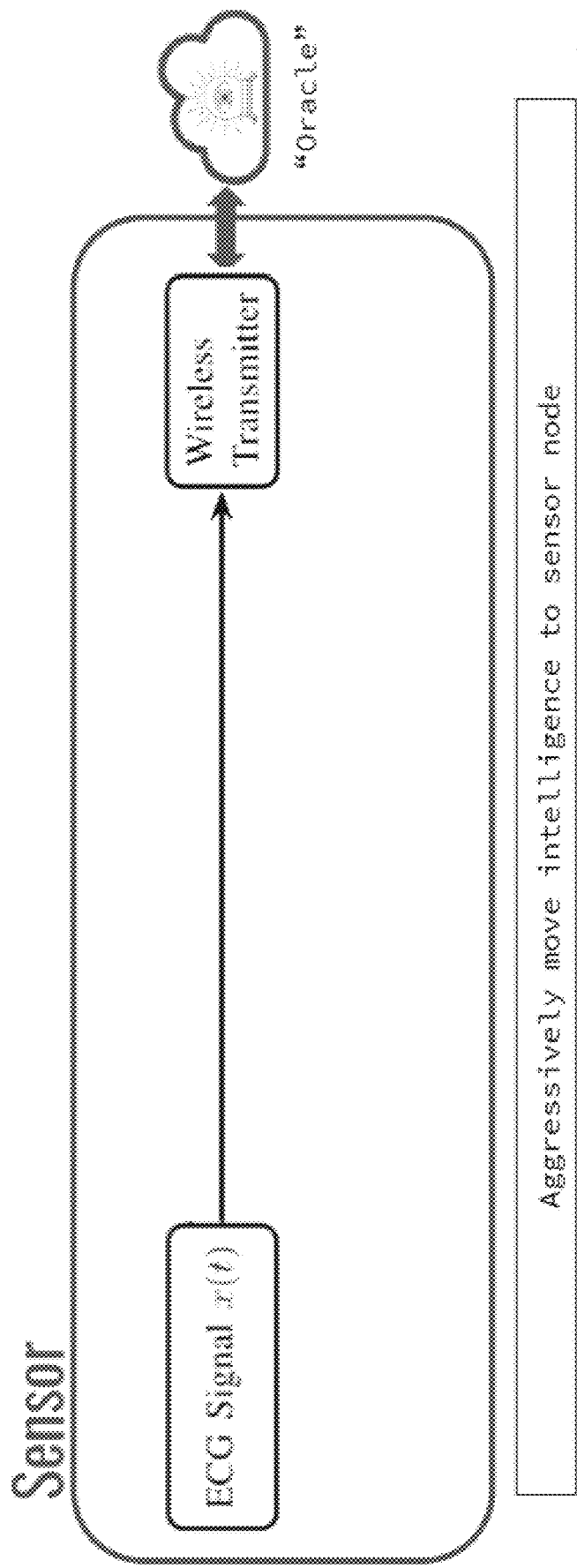

FIG. 9 shows a simple diagram of their system where the sensor reads an ECG Signal x(t) and transfers data to a wireless transmitter transmitting to an "Oracle."

Figure 10:
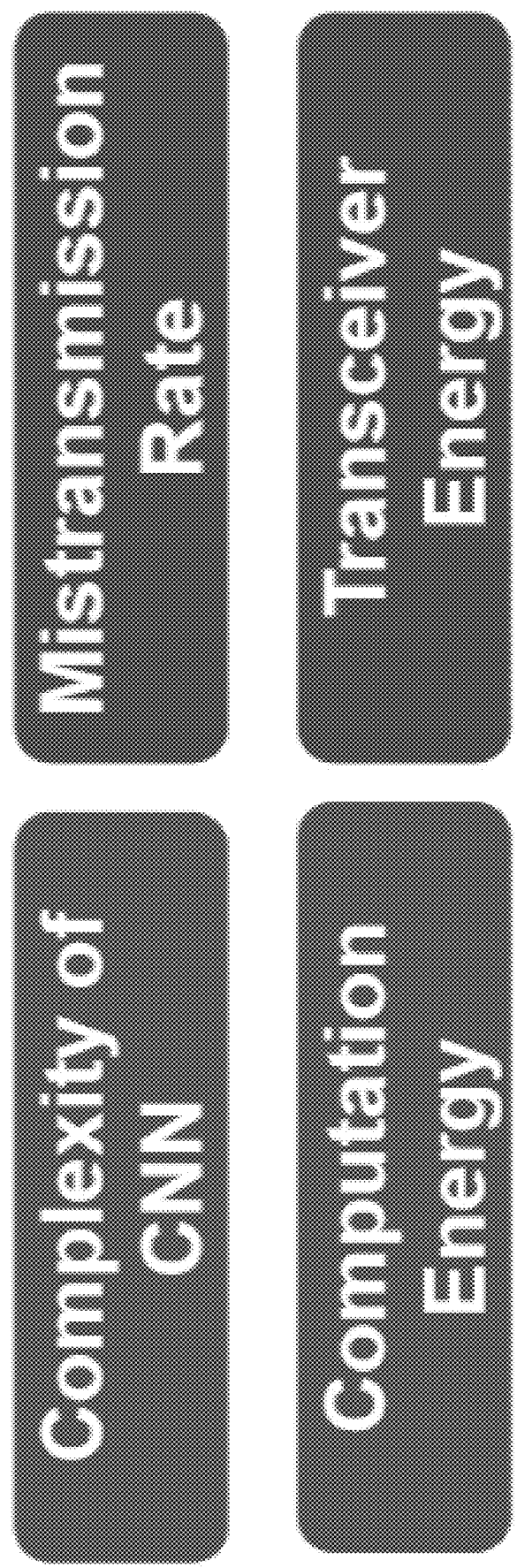

FIG. 10 shows some of the points of focus that were considered while optimizing this invention: Complexity of CNN, Computation energy, Mistransmission rate, and Transceiver energy.

Figure 11:
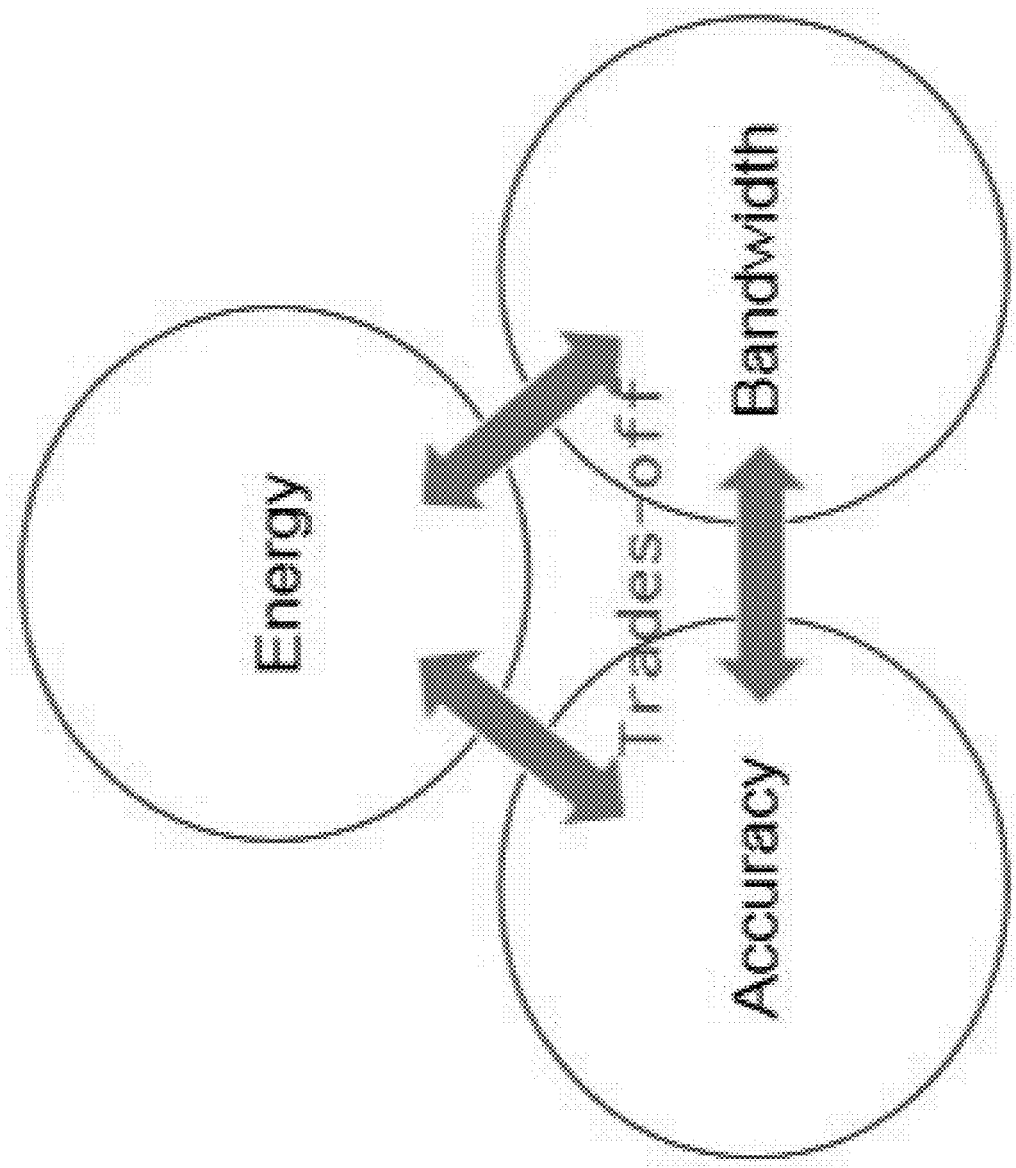

FIG. 11 shows a diagram of the tradeoffs of optimization in this invention between energy, accuracy, and bandwidth.

FIG. 12 shows two metrics that were used to minimize the bandwidth utilization and the mistransmission rate over an ECG signal time series.

Figure 13:
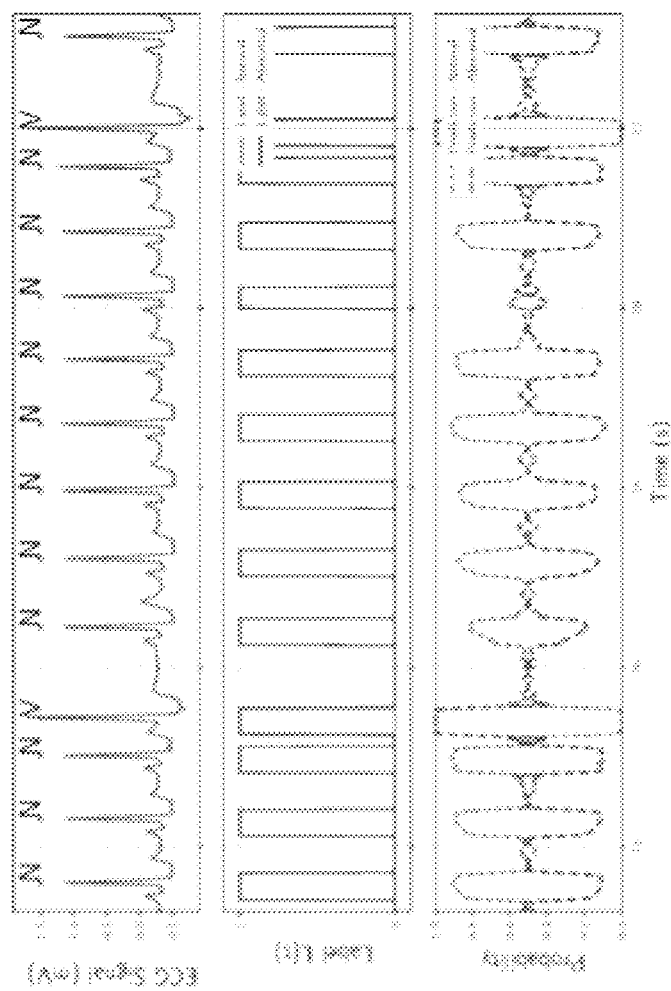

FIG. 13 shows inference results on MITDB record number 105 vie CNN which has 137,510 parameters (see FIG. 3).

Figure 14:
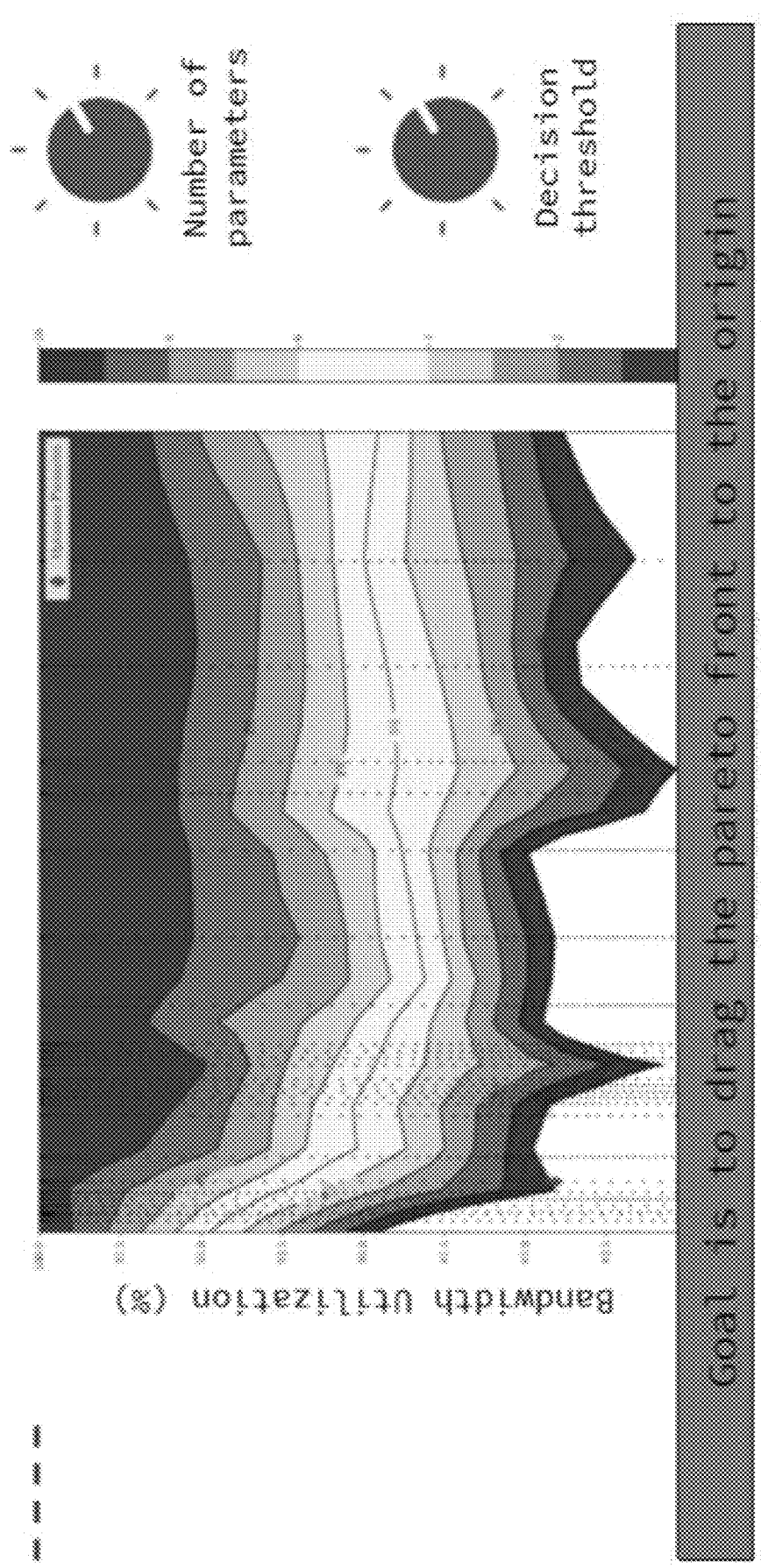

FIG. 14 shows a contour plot of the mistransmission rate among 6 test records (see FIG. 5) in relation to the number of parameters in the CNN and the bandwidth utilization.

FIG. 15 shows a table of various CNN topologies tested and the energy savings, decision threshold, and bandwidth utilization across each one.

Figure 16:
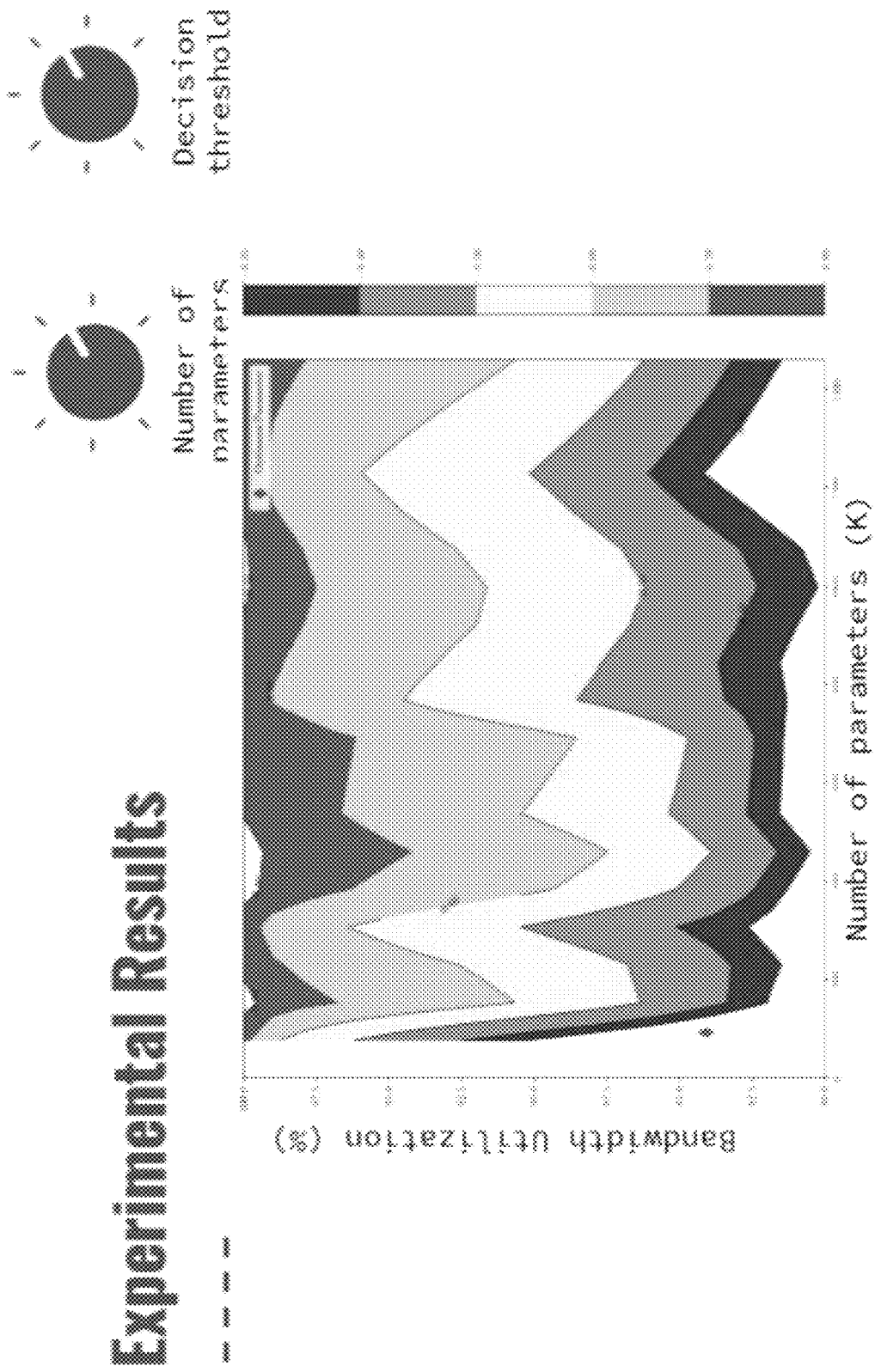

FIG. 16 shows a contour plot of the decision threshold among 6 test records (see FIG. 5) in relation to the number of parameters and the bandwidth utilization.

DETAILED DESCRIPTION OF THE INVENTION

Following is a list of elements corresponding to a particular element referred to herein: A sensor may acquire an ECG signal and wirelessly transmits it to a server. Additionally, it is assumed that only the abnormal rhythms need to be transmitted for further interpretation by either an expert or a machine learning model. Intuitively, transporting the whole signal to a server does not require any computation at the sensor, but imposes a high traffic load to the wireless channel, whose capacity is often limited. Compression can reduce traffic. However, compression in a narrow sense assumes lossless recovery of all the rhythms whose completeness may not be necessary in the application. Arguably, adopting lossy compression can aggressively reduce channel usage while taking a toll on the overall quality of the recovered signal and the final classification accuracy on the server end.

The technique proposed whose schematic is represented in FIG. 1 takes the different approach of pre-selecting at the sensor abnormal rhythms. A neural network is followed by a decision logic whose objective is to discard all rhythms deemed normal. Clearly, the sensor cannot afford to execute the full-fledged classifier, whose use would result in no accuracy loss and minimal channel usage. We, then, explore the tradeoff between the computational complexity pushed to the sensor, and the performance of the system. Four metrics are explicitly considered: (a) overall accuracy of the classification process, (b) bandwidth utilization, (c) pre-selection accuracy, and (d) energy usage.

Formal definitions of the signals and performance metrics mentioned earlier are provided below. Signal label pairs consisting of a digitized ECG signal and samplewise anomaly labels annotated by ECG specialists are considered:

$$x(t)=[x_1,x_2,x_3,x_4,x_5,\ldots,x_n] \tag{1}$$

$$L(t)=[(1,0),(0,1),(1,0),(0,1),(0,1),\ldots,(1,0)] \tag{2}$$

where brackets denote a time series of discrete samples. Labels in the following discussion are expected to take a 2-tuple format where abnormality and normality are indicated by the first and the second element, respectively. For abnormal samples, say $x_1$ in Eq. 3, the label is (1,0). On the other hand, (0,1) are tagged on normal samples such as $x_3$. Note that not all samples are annotated. Therefore, some samples may have (0,0) meaning they are neither tagged positive nor negative. Acquisition is followed by decision logic, denoted by $\mathcal{D}\{\bullet\}$ which selects positive samples from x(t) and output transmitting time series $x_T(t)$. For example, if samples $x_2$, $x_4$, and $x_5$ are predicted to be associated with normal rhythms, $\mathcal{D}\{\bullet\}$ replaces them with a special symbol $\phi$ to command wireless transmitter not to transmit those samples. The following equation shows the corresponding output of decision logic if the realization of x(t) in Equation (1) is the input:

$$x_T(t)=\mathcal{D}\{x(t)\}=[x_1,\phi,x_3,\phi,\phi,\ldots,x_n]. \tag{3}$$

Intuitively, the bandwidth utilization $b_{tx}$ of an ECG frame is defined as a ratio of valid samples between raw signal $x_T(t)$ and transmitted signal x(t)

$$b_{tx} = \frac{|\{x_i : x_i \in x_T(t) \wedge x_i \neq \phi\}|}{|\{x_i : x_i \in x(t)\}|}. \tag{4}$$

To evaluate the loss of sensitivity caused by dropped positive samples, the ground truth L(t) is used to define the mistransmission rate $\epsilon_{mt}$ as the ratio of positive samples between $x_T(t)$ and in x(t), that is, $$\epsilon_{mt} = \frac{|\{x_i : x_i \in x_T(t) \wedge L(t_i) - (1, 0)\}|}{|\{x_i : x_i \in x(t) \wedge L(t_i) - (1, 0)\}|}. \tag{5}$$

To justify the new system architecture, the following question arises: Will the energy savings in RF transmission be greater than the cost of running an extra CNN?

To address this question, this section proposes an analytical model for energy consumption that takes into consideration both RF transmission and CNN inference [11].

TABLE I

NORMALIZED ENERGY COSTS FOR CRITICAL OPERATIONS IN UNIFIED ENERGY MODEL (ASSUME a AND b ARE 8-BIT NUMBERS)

| Operation | Symbol | Norm. Energy | Energy |
|---|---|---|---|
| DRAM R/W | $E_d$ | 4000× | 320 pJ |
| Global Buffer R/W | $E_g$ | 15× | 1.2 pJ |
| Inter-PE Comm. | $E_p$ | 5× | 400 fJ |
| Register File R/W | $E_r$ | 2.5× | 200 fJ |
| a + b | $E_a$ | $10^{-2}$× | 0.8 fJ |
| a × b | $E_m$ | 1× | 80 fJ |
| RF Transmission | $E_{tx}$ | $10^6$× | 80 μJ |

If the RF transmitter energy model described in [12] is considered, transmitter energy consumption $E_{tx}$ can be broken down into two components: transmitted energy $E_t$, and dissipated energy $E_h$, i.e. waste heat, as in $$E_{t,r}=E_t+E_h=(P_t+P_h)T_{tr}=P_{tx}T_{tx} \tag{6}$$

where $T_{tx}$ is the accumulated time for active signaling, i.e. $x_T(t)\neq\phi$. Since a body area network (BAN) application is targeted, the transmitter-receiver distance is set to d=10 m. For simplicity, 8-DPSK is selected, which transports 3 bits per symbol, as the modulation scheme. Transmission energy cost is approximately 10 μJ/bit, in the case of the same set of system design parameters as in [12].

In order to estimate the energy consumption per inference, an energy model analogous to proposed by Chen et. al. in [13] is used. The energy costs associated with each operation are listed in Table I where 8-bit fixed-point numbers are assumed in each operation. Then, the average energy $\varepsilon$ for the proposed system to process an ECG sample can, then, be computed as $$\varepsilon \approx l_f \left( \left( \gamma_{wd}^{-1} \vec{1}_l \cdot \vec{n}_c + \gamma_{dd}^{-1} \right) E_d + \left( \gamma_{wg}^{-1} \vec{1}_l \cdot \vec{n}_c + \gamma_{dg}^{-1} \right) E_g + \left( \gamma_{wp}^{-1} \vec{1}_l \cdot \vec{n}_c + \gamma_{dp}^{-1} \right) E_p + \right. \tag{7}$$
$$\left. \left( \gamma_{wr}^{-1} \vec{1}_l \cdot \vec{n}_c + \gamma_{dr}^{-1} \right) E_r + \vec{1}_l \cdot \vec{n}_c (E_a + E_m) \right) + b_{tx} E_{tx} = E_{comp} + b_{tx} E_{tx}$$

where • denotes vector inner product, $l_f$ is the length of filter; $\vec{1}_l$ denotes an all one vector of length l; $\vec{n}_c$ is the number of channels in the CNN. Data and weight reuses are modeled by $\gamma$ factors: the first character in subscript denotes data (d) and weight (w), while the second subscript denotes a particular memory hierarchy. Specifically $\gamma_{dd}$, $\gamma_{dg}$, $\gamma_{dp}$, and $\gamma_{dr}$, corresponds to data reuse at DRAM (d), global buffer (g), array (p), and register files (r), respectively. Note Eq. 7 represents the energy cost to generate a single output.

The relative reduction in energy over a naive system is $$\Delta \varepsilon = \frac{\varepsilon_{naive} - \varepsilon}{\varepsilon_{naive}} = \frac{E_{tx} - \varepsilon}{E_{tx}}, \tag{8}$$

a metric that will be used in Section V to assess the savings in energy consumption through the proposed approach.

In the following, the components of the system are described in detail.

Intuitively, a neural network as complex as that used at the remote device to perform final classification would enable a "perfect" selection of anomalous signal sections. In fact, as the two classifiers have the same output, only positive cycles would be selected for transmission, thus minimizing channel usage without any accuracy degradation. Clearly, such a complex neural network cannot be executed within wearable sensors. Therefore, a range of parameters corresponding to different levels of complexity are explored—and thus energy consumption and selection accuracy—for DNNs deployed on wearable sensors.

A total of 26 variants of customized sequence were trained to sequence CNN (S2SCNN) models to translate single-lead ECG signals into sample-wise annotation of arrhythmia. FIG. 2 shows a representative version, which has 800,010 parameters, composed of 4 convolution (CONV) modules. The output of the CNN consists of two probability estimates $\hat{y}a$, and $\hat{y}n$, indicating probabilities of abnormality and normality, respectively. Each CONV module consists of a 64-channel 1D convolution filter which has a filter length of 64, a batch normalization layer, rectified linear (ReLU) activation layer, and a dropout layer set to a 25% dropout rate. Since the training data only has labels marked on QRS complexes, at the output of each network, a softmax layer is employed to enable generation of the most decisive predictions by the CNN.

All CNNs are implemented in Keras with Tensorflow backend. Training is performed de novo with random initialization of weights. The Adam optimizer is used with gradient clipping enabled and a mini-batch size of 128. The initial learning rate is set to 1×10−3 and reduced by tenfold when validation loss levels off. Convergence can be reached within 20 training epochs in half an hour on the nVidia 2080Ti GPU.

Signal compression is realized by the decision logic, which takes the raw signal x(t) and the outputs of the neural network to determine whether sections of the signal are transmitted or not. The logic will selectively transmit samples if the output of the neural network exceeds threshold $\tau$. The transfer function of the decision logic can be formulated by $$x_T(t) = \begin{cases} x(t) & \text{if } \hat{y}_a(t) - \hat{y}_a(t) >= -\tau \\ \phi & \text{otherwise} \end{cases} \tag{9}$$

Threshold $\tau$ is a system design parameter which allows adjustment on sensitivity. Lower $\tau$ is more conservative in generating negative predictions. Also, reducing $\tau$ implies more data will be transmitted.

TABLE II

Performance Summary of CNN Variants.

| Parameters | #CONV | Channels $\vec{n}_c$ | AUC | TPR |
|---|---|---|---|---|
| 1460160 | 4 | [106, 106, 106, 2] | 0.862 | 0.683 |
| 1224441 | 4 | [97, 97, 97, 2] | 0.863 | 0.799 |
| 1032321 | 4 | [89, 89, 89, 2] | 0.868 | 0.729 |
| 856585 | 4 | [81, 81, 81, 2] | 0.867 | 0.782 |
| 800010 | 5 | [64, 64, 64, 64, 2] | 0.849 | 0.737 |
| 697233 | 4 | [73, 73, 73, 2] | 0.864 | 0.759 |
| 537546 | 4 | [64, 64, 64, 2] | 0.870 | 0.742 |
| 413010 | 4 | [56, 56, 56, 2] | 0.880 | 0.759 |
| 343495 | 4 | [51, 51, 51, 2] | 0.863 | 0.762 |
| 330360 | 4 | [50, 50, 50, 2] | 0.870 | 0.779 |
| 317481 | 4 | [49, 49, 49, 2] | 0.860 | 0.777 |
| 304858 | 4 | [48, 48, 48, 2] | 0.867 | 0.813 |
| 280380 | 4 | [46, 46, 46, 2] | 0.845 | 0.575 |
| 268525 | 4 | [45, 45, 45, 2] | 0.869 | 0.676 |
| 256926 | 4 | [44, 44, 44, 2] | 0.864 | 0.753 |
| 245583 | 4 | [43, 43, 43, 2] | 0.855 | 0.778 |
| 234496 | 4 | [42, 42, 42, 2] | 0.844 | 0.759 |
| 213090 | 4 | [40, 40, 40, 2] | 0.882 | 0.795 |
| 137706 | 4 | [32, 32, 32, 2] | 0.874 | 0.724 |
| 91920 | 4 | [26, 26, 26, 2] | 0.864 | 0.769 |
| 72010 | 3 | [32, 32, 2] | 0.865 | 0.836 |
| 60805 | 4 | [21, 21, 21, 2] | 0.863 | 0.731 |
| 48526 | 3 | [26, 26, 2] | 0.877 | 0.716 |
| 36090 | 4 | [16, 16, 16, 2] | 0.870 | 0.724 |
| 32476 | 3 | [21, 21, 2] | 0.842 | 0.819 |
| 19626 | 3 | [16, 16, 2] | 0.858 | 0.719 |

AUC: Area under ROC curve;
TPR: true positive rate when $\tau = 0$

TABLE III

RELATIVE ENERGY SAVINGS ON DIFFERENT RECORDS IF 1% $\epsilon_{mt}$ IS GUARANTEED

| Record | $\Delta \varepsilon$ (%) | $\tau$ | $b_{tx}$ (%) |
|---|---|---|---|
| 105 | 33.91 | −0.14 | 59.71 |
| 1121a | 18.12 | 0.03 | 75.50 |
| 210 | 13.47 | −0.44 | 80.15 |
| 114 | 8.48 | −0.56 | 85.15 |
| ECG-P18-02 | −3.65 | −0.72 | 97.28 |
| 107 | −4.75 | −0.14 | 98.37 |
| 124 | −5.65 | −0.81 | 99.28 |
| Mean | 8.56 | −0.40 | 85.06 |
| Max | 33.91 | −0.03 | 99.28 |
| Min | −5.65 | −0.81 | 59.71 |

To evaluate the proposed system, energy efficiency in recording arrhythmia which is evident from uneven heartbeats in the is maximized ECG. In some embodiments, the CNN may be trained with a dataset comprising records of a plurality of heart cycles. Multiple ECG datasets were obtained from PhysioNet and Telemetric and Holter ECG warehouse (THEW) [15]. Five specific datasets are combined to obtain a 205-record dataset for CNN training and system evaluation. Each of the records has associated labeling information that is compliant to ANSI/AAMI EC57 standard (AAMI). The dataset is then split into training, development, and test subsets. Each of them has 184, 10, and 11 records, respectively. Records from the same subject do not overlap or duplicate across different datasets. According to Luz et. al. [16], (modified) lead II (II/MLII) is selected to be the most informative feature for arrhythmia detection.

Abnormal rhythms are derived from disjunction of S, V, F, and Q categories; Normal rhythms are marked by label N. Indexes of both types of heartbeats are converted into two impulse trains $\delta_a$(t) and $\delta_n$(t), respectively. To account for average PR interval and QRS complex duration, the intervals advancing and lagging R-peak 0.2 seconds and 0.1 seconds are both assumed to share the same label assigned to corresponding R-peak.

Three system parameters, namely 1) topology of CNN p, 2) computation resource parameters $\gamma$, and 3) communication system parameters t, determine the overall system performance which is defined by application performance $\in_{mt}$ and energy cost $\varepsilon$. Here, 2) and 3) are assumed to be fixed and orthogonal to the CNN parameters. On dataset D, the problem of finding the optimal system parameters can be formulated as $$\hat{p} = \underset{p \in \mathcal{P}}{\operatorname{argmin}} \; r_p[CNN_p(\mathcal{D})]P_{tx,t} + \sigma[CNN_p(\mathcal{D})]E_{comp,\gamma} \quad (10)$$

subject to $\epsilon_{mt} < T$, where $r_p[CNN(\mathcal{D})]$ and $\sigma[CNN(\mathcal{D})]$ denote the rate of positive calls of CNN and the total amount of computations, respectively. Grid search on parameter space $\mathcal{P}$ was used to determine the best configuration of p which is derived numerically in the next section.

Table III summarizes the energy savings as computed in Eq. 8. Only the best performing CNN (indicated by a*in FIG. 4) is represented in the table while simulations are performed based on all variants of CNNs listed in Table II. The threshold is set to allow at most 1% of mistransmission rate $\in_{mt}$.

Contour plots of the mistransmission rate are shown in FIG. 5a with corresponding threshold $\tau$ in FIG. 5b. The contours are triangularized on mesh grids of $b_{tx}$ and number of parameters in the CNN. Note that setting the threshold to −1 results in $\in = 0\%$ as all samples are transmitted. On the ordinate, where the number of parameters is zero, data points are computed based on "stochastic transmitter" assumption. The stochastic transmitter is defined to randomly drop samples for bandwidth saving. Asymptotic limit of the mistransmission rate when the number of parameters approaches zero, i.e. no CNN in the system, is estimated under this assumption.

As summarized in FIG. 4, the overall best performance can be achieved with the CNN which has 91,920 parameters. This result is consistent with the highlighted design point closest to the origin in FIG. 5a. The energy saving is a direct result of the CNN performance.

A new technique that leverages a lightweight DNN is proposed to minimize energy consumption on wearable ECG sensors by selectively transmitting only the informative parts of an acquired ECG signal. A unified energy model for DNN-assisted embedded systems is also formulated. The extensive experiments on real-world datasets demonstrate that the proposed methodology locates the optimal CNN hyperparameters that minimizes the overall energy cost, while maintaining classification performance above a predefined threshold, making this a viable approach for deploying DNNs on resource-constrained sensors.

The following description sets forth numerous specific details (e.g., specific configurations, parameters, examples, etc.) of the disclosed embodiments, examples of which are illustrated in the accompanying drawings. It should be recognized, however, that such description is not intended as a limitation on the scope of the disclosed embodiments, but is intended to elaborate upon the description of these embodiments. It will be evident to a person of ordinary skill in the art that the present invention can be practiced without every specific detail described infra. Moreover, well-known methods, procedures, components, and circuits have not been described in detail so as not to unnecessarily obscure aspects of the embodiments of the present invention.

It is fully contemplated that the features, components, and/or steps described with respect to one embodiment may be combined with the features, components, and/or steps described with respect to other embodiments of the present disclosure. To avoid needless descriptive repetition, one or more components or actions described in accordance with one exemplary embodiment can be used or omitted as applicable from other embodiments. For the sake of brevity, the numerous iterations of these combinations will not be described separately. The same reference numbers may be used to refer to the same or similar elements in different drawings. Alternately, different reference numbers may be used to refer to the same or similar elements in the drawings of different embodiments. Any distinction of an element's reference number in one embodiment from another is not limiting in any way, does not suggest that elements of one embodiment could not be combined with or substituted for elements in another embodiment, and (most importantly) is specifically intended only to facilitate the matching of elements in the disclosure to their corresponding claim recitations.

Embodiments within the scope of the present invention may comprise non-transitory computer-readable media for storing computer-executable instructions. Instructions that cause at least one processing circuit to perform one or more operations are "computer-executable." The term "non-transitory" is used herein to distinguish two distinctly different kinds of computer-readable media: physical storage media that stores computer-executable instructions and transmission media that carries computer-executable instructions. Physical storage media includes RAM and other volatile types of memory; ROM, EEPROM and other non-volatile types of memory; CD-ROM, CD-RW, DVD-ROM, DVD-RW, and other optical disk storage; magnetic disk storage or other magnetic storage devices; and any other tangible medium that can store computer-executable instructions that can be accessed and processed by at least one processing circuit.

Transmission media can include signals carrying computer-executable instructions over a network to be received by a general-purpose or special-purpose computer. Embodiments of the present invention expressly (by exemplary recitation such as "non-transitory") exclude signals carrying computer-executable instructions. However, it should be understood that once a signal carrying computer-executable instructions is received by a computer, the type of computer-readable storage media transforms automatically from transmission media to physical storage media. This transformation may even occur early on in intermediate memory such as (by way of example and not limitation) a buffer in the RAM of a network interface card, regardless of whether the buffer's content is later transferred to less volatile RAM in the computer. Thus, devices that merely repeat a signal are contemplated by the embodiments of the present invention, even though the media that carry the signal between such devices and the signal itself are expressly not included within the claim scope. Thus, it should be understood that "non-transitory computer-readable storage media" is used herein instead of simply "physical storage media" or "physical computer-readable storage media" in order to underscore that even transmission media necessarily involves eventual transformation into physical storage media and to therefore capture all embodiments where the computer-readable instructions are stored in physical storage media—even if only temporarily before transforming back into transmission media.

Where two or more elements are said to be "coupled," the meaning shall include (in addition to configurations where the elements directly operate with each other because they are joined) configurations where the elements indirectly operate with each other (e.g., through one or more intermediate elements) so long as there is a link.

In some embodiments, a wearable echocardiographic (ECG) device may comprise an ECG sensor, a transmitter, a processor for executing instructions, RAM, and hard disk memory upon which are stored computer-executable instructions for a convoluted neural network (CNN). In some embodiments, when executed by the processor, the instructions for the CNN may cause the processor to perform operations. The operations may comprise receiving an uncompressed sample of a continuous ECG signal from a sensor. In some embodiments, the CNN may assess the probability that the received sample is abnormal as well as assess the probability that the received sample is normal. In some embodiments, the CNN may determine whether to transmit the uncompressed sample based on whether a threshold of abnormality is less than or equal to the difference between the first probability and the second probability.

In some embodiments, the CNN may be trained with a dataset comprising at least 205 records of heart cycles. In some embodiments, the CNN may have 91,920 parameters. In some embodiments, 1% or less of the samples determined by the CNN to be normal may actually be abnormal. In some embodiments, the sample may encompass a plurality of heart cycles.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

The invention claimed is:

1. An energy-efficient method of monitoring a continuous physiological signal while maintaining high accuracy, the method comprises:
   a) receiving, by a convolutional neural network (CNN), one or more uncompressed samples of the continuous physiological signal from a sensor;
      wherein the sensor comprises a memory unit comprising the CNN;
   b) determining, by the CNN, a first probability that the each uncompressed sample of the one or more uncompressed samples is abnormal and a second probability that the uncompressed sample is normal;
   c) determining whether or not to transmit the one or more abnormal uncompressed samples using a threshold strategy that utilizes the first probability and the second probability; and
   d) transmitting the one or more abnormal uncompressed samples based on said determination;
      wherein the CNN has been trained with a dataset comprising at least 205 records;
      wherein the CNN has 91,920 parameters;
      wherein the CNN comprises a 64-channel 1-dimensional convolution filter having a filter length of 64, a batch normalization layer, a rectified linear activation layer, a dropout layer set to a 25% dropout rate, and a softmax layer.

2. The method of claim 1, wherein the dataset comprises records of a plurality of heart cycles.

3. An energy-efficient system of monitoring an electrocardiogram (ECG) sensor while maintaining high accuracy, wherein the system comprises:
   a) the ECG sensor comprising a memory unit comprising a convolutional neural network (CNN);
   b) a transmitter;
   c) a processor;
   d) a Random Access Memory (RAM); and
   e) an external memory, wherein the external memory comprises instructions for:
      i) receiving, by the CNN, one or more uncompressed samples of a continuous ECG signal from the ECG sensor,
      ii) determining, by the CNN, a first probability that the each uncompressed sample of the one or more uncompressed samples is abnormal and a second probability that the uncompressed sample is normal,
      iii) determining whether or not to transmit the one or more abnormal uncompressed samples using a threshold strategy that utilizes the first probability and the second probability; and
      iv) transmitting the one or more abnormal uncompressed samples based on said determination;
   wherein the CNN has been trained with a dataset comprising at least 205 records;
   wherein the CNN has 91,920 parameters;
   wherein the CNN comprises a 64-channel 1-dimensional convolution filter having a filter length of 64, a batch normalization layer, a rectified linear activation layer, a dropout layer set to a 25% dropout rate, and a softmax layer.

4. The system of claim 3, wherein the dataset comprises records of a plurality of heart cycles.

5. A non-transitory computer-readable storage medium having computer-executable instructions recorded thereon for an energy-efficient convolutional neural network (CNN)-driven electrocardiogram (ECG) monitor that, when executed by at least one processing circuit, perform a computer process, wherein the computer process comprises:

a) receiving, by a CNN, one or more uncompressed samples of a continuous ECG signal from a sensor;
wherein the sensor comprises a memory unit comprising the CNN;
b) determining, by the CNN, a first probability that the each uncompressed sample of the one or more uncompressed samples is abnormal and a second probability that the uncompressed sample is normal;
c) determining whether or not to transmit the one or more abnormal uncompressed samples using a threshold strategy that utilizes the first probability and the second probability; and
d) transmitting the one or more abnormal uncompressed samples based on said determination;
wherein the CNN has been trained with a dataset comprising at least 205 records;
wherein the CNN has 91,920 parameters;
wherein the CNN comprises a 64-channel 1-dimensional convolution filter having a filter length of 64, a batch normalization layer, a rectified linear activation layer, a dropout layer set to a 25% dropout rate, and a softmax layer.

6. The non-transitory computer-readable storage medium of claim 5, wherein a duration of the uncompressed sample comprises a plurality of heart cycles.

* * * * *